US010245274B2

(12) United States Patent
O'Malley et al.

(10) Patent No.: US 10,245,274 B2
(45) Date of Patent: *Apr. 2, 2019

(54) CHITOSAN-BASED MATRICES AND USES THEREOF (71) Applicant: THE TRUSTEES OF THE UNIVERSITY OF PENNSYLVANIA, Philadelphia, PA (US)

(72) Inventors: Bert W. O'Malley, Villanova, PA (US); Daqing Li, Wynnewood, PA (US); David Paulson, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/167,136

(22) Filed: May 27, 2016

(65) Prior Publication Data

US 2016/0271148 A1    Sep. 22, 2016

Related U.S. Application Data

(62) Division of application No. 12/747,452, filed as application No. PCT/US2008/086099 on Dec. 9, 2008, now abandoned.

(60) Provisional application No. 60/996,877, filed on Dec. 10, 2007.

(51) Int. Cl.
| | |
|---|---|
| *A61K 9/00* | (2006.01) |
| *A61K 9/06* | (2006.01) |
| *A61K 9/16* | (2006.01) |
| *A61K 47/10* | (2017.01) |
| *A61K 47/24* | (2006.01) |
| *A61K 47/34* | (2017.01) |
| *A61K 47/36* | (2006.01) |
| *A61K 31/573* | (2006.01) |

(52) U.S. Cl.
CPC .......... *A61K 31/573* (2013.01); *A61K 9/0019* (2013.01); *A61K 9/0046* (2013.01); *A61K 9/06* (2013.01); *A61K 9/1652* (2013.01); *A61K 47/10* (2013.01); *A61K 47/24* (2013.01); *A61K 47/34* (2013.01); *A61K 47/36* (2013.01)

(58) Field of Classification Search
USPC ......................................................... 524/115
See application file for complete search history.

(56) References Cited

U.S. PATENT DOCUMENTS

| | | | |
|---|---|---|---|
| 4,474,752 A | 10/1984 | Haslam et al. | |
| 4,957,674 A | 9/1990 | Ichitsuka et al. | |
| 6,344,488 B1 * | 2/2002 | Chenite ................ | A61K 9/0019 424/422 |
| 2003/0158302 A1 * | 8/2003 | Chaput ................ | A61K 9/0019 524/115 |

OTHER PUBLICATIONS

Garduno-Anaya et al., "Dexamethasone Inner Ear Perfusion by Intratympanic Injection in Unilateral Meniere's Disease: A Two-year Prospective, Placebo-Controlled, Double-blind, Randomized Trial." Otolaryngology-Head and Neck Surgery (2005) 133, 285-294.*
Salt et al., "Local inner-ear drug delivery and pharmacokinetics." Drug Discovery Today vol. 10, No. 19, Oct. 2005.*
Chenite et al., "Characterization of thermosensitive chitosan gels for the sustained delivery of drugs." International Journal of Pharmaceutics 203 (2000) 89-98. (Year: 2000).*
Ma et al., "Topical treatment with growth factors for tympanic membrane perforations: progress towards clinical application" Acta Otolaryngol 2002: 122; 586-599.
Buchwald et al. "Long-term, continuous intravenous heparin administration by an implantable infusion pump in ambulatory patients with recurrent venous thrombosis."Surgery 88:507 (1980).
Saudek et al."A preliminary trial of the programmable implantable medication system for insulin delivery." N. Engl. J. Med. 321:574 (1989).
Goodson, in Medical Applications of Controlled Release, supra, vol. 2, pp. 115-138 (1984).
Langer, "New methods of drug delivery", Science 249:1527-1533 (1990).
Katre et al. "Chemical modification of recombinant interleukin 2 by polyethylene glycol increases its potency in the murine Meth A sarcoma model" Proc Natl Acad Sci U S A. 84(6):1487-91. Mar. 1987.
Sefton, "Implantable pumps", CRC Crit. Ref. Biomed. Eng. 14:201 (1987).
Johnsen et al., <<Isolation, characterization and heterologous expression of a novel chitosanase from *Janthinobacterium* sp. strain 4239 *Microbial Cell Factories* 2010, 9:5.
Chenite et al., "Rheological characterization of thermogelling chitosan/glycerol-phosphate solution", Carbohydrate Polymers 46 (2001), 39-47.
Park et al., "Environment-sensitive hydrogels for drug delivery", Advanced Drug Delivery Reviews 53 (2001), 321-339.

* cited by examiner

*Primary Examiner* — Walter E Webb
(74) *Attorney, Agent, or Firm* — Mark S. Cohen; Pearl Cohen Zedek Latzer Baratz LLP (57) ABSTRACT

This invention relates a controlled release delivery composition for an otorhinolaryngology and otorhinolaryngology-associated pathology, conditions, indications or their combination, Head and Neck associated pathology conditions, indications or their combination, or their combination, using a chitosan-glycerophosphate (CGP) hydrogel and an agent or a bio-materials. Additionally, provided methods of treating an otorhinolaryngology and otorhinolaryngology-associated pathology, conditions, indications or their combination, Head and Neck associated pathology conditions, indications or their combination, or their combination.

13 Claims, 3 Drawing Sheets

CHITOSAN-BASED MATRICES AND USES THEREOF

CROSS REFERENCE TO RELATED APPLICATIONS

This application is a divisional of U.S patent application Ser. No. 12/747,452, filed Jan 12, 2011, which is a national stage application of PCT application PCT/US2008/86099, filed Dec 9, 2008, which claims priority to U.S. Provisional Patent Application 60/996,877, filed Dec 10, 2007, all of which are hereby incorporated in their entirety.

FIELD OF INVENTION

This invention is directed to a controlled release delivery composition for pathologies associated with Otorhinolaryngology and Head and Neck.

BACKGROUND OF THE INVENTION

The Effective medical treatment of inner ear disease depends upon achieving therapeutic concentrations of medications, such as dexamethasone or gentamicin, within the fluids and tissues of the inner ear. Drugs delivered to the inner ear are commonly administered systemically via the oral, intravenous, or intramuscular routes. However, systemic drug administration for focal disease of the inner ear is not ideal as this does not meet an important pharmacological principal in which local administration is preferred for local pathological processes.

Systemic drug administration increases the likelihood of systemic toxicities and side effects and creates an inequality in drug concentration with higher circulating levels in the serum but lower local levels at the inner ear where the drug is needed. Relatively large doses of a medication are therefore required to overcome the systemic volume of distribution in order to achieve a therapeutic drug concentration in the inner ear. In addition to the inherent risk of toxicities, responses to systemic administration vary considerably between patients. This is due to inter-dose variability, differences in systemic volume of distribution, variability in the ability of a given drug to cross the blood-inner ear barrier, and factors affecting the half-life of the drug such as peripheral drug metabolism and drug clearance.

Intratympanic injection of streptomycin for the treatment of intractable vertigo in patients with Meniere's disease resulted in profound hearing loss in a significant proportion of patients. However, reported success in ameliorating Meniere's symptomology with intratympanic drug administration helped to popularize the concept of local drug administration to the inner ear. Indeed, it has become routine for otolaryngologists to perform intratympanic injections, and the efficacy of this approach versus systemic drug administration has been confirmed for various clinical indications.

However, there remains a considerable amount of variability in clinical outcomes among those patients treated with intratympanic injections. Several factors account for this variability. Drugs enter the fluids of the inner ear by diffusing across the round window membrane (RWM), the major site of absorption of medications from the middle ear into the inner ear. Unfortunately, large portions of the administered medication do not come into contact with the RWM. This portion of drug is instead absorbed by the mucosa of the middle ear or evacuated from the middle ear space by the eustachian tube. In either case, the drug is unavailable to diffuse into the inner ear. Therefore, the concentration of drug in the inner ear depends greatly upon the drug coming into contact with the RWM.

SUMMARY OF THE INVENTION

In one embodiment, the invention provides a composition for controlled release delivery, comprising: a chitosan-glycerophosphate (CGP) hydrogel; and one or more agent effective in the treatment of otorhinolaryngology-associated pathology, or Head and Neck associated pathology. In another embodiment the one or more agent are bio-materials.

In another embodiment, the invention further provides a method of treating an otorhinolaryngology-associated pathology, or Head and Neck associated pathology in a subject, comprising the step of inserting a composition comprising a chitosan-glycerophosphate (CGP) hydrogel and one or more agent in a predetermined region of said subject, wherein the agent is effective in the treatment of otorhinolaryngology-associated pathology, or Head and Neck associated pathology. In another embodiment the on or more agent are bio-materials.

In one embodiment, the invention provides a method of treating an otorhinolaryngology and otorhinolaryngology-associated pathology, conditions, indications or their combination, or Head and Neck associated pathology conditions, indications or their combination, in a subject, comprising the step of inserting a composition comprising a chitosan-glycerophosphate (CGP) hydrogel and one or more agent in a predetermined region of said subject, wherein the agent is effective in the treatment of otorhinolaryngology and otorhinolaryngology-associated pathology, conditions, indications or their combination, or Head and Neck associated pathology conditions, indications or their combination.

In one embodiment, the invention provides a method of reducing symptoms associated with an otorhinolaryngology and otorhinolaryngology-associated pathology, conditions, indications or their combination, Head and Neck associated pathology conditions, indications or their combination, or their combination, in a subject, comprising the step of inserting a composition comprising a chitosan-glycerophosphate (CGP) hydrogel and an agent, bio-materials and their combination in a predetermined region in a subject.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will be better understood from a reading of the following detailed description taken in conjunction with the drawings in which like reference designators are used to designate like elements, and in which:

FIG. 4 shows normal hearing following CGP-Dex-Hydrogel Placement. 4a) The solid line represents the pre-operative baseline ABR value of the sham surgery group. There was a 5 to 20 dB increase in hearing thresholds across frequencies in the immediate post-operative period (dashed line). By post-operative day 10, the hearing thresholds returned to baseline levels (dotted line). At the conclusion of the experiment, there was no statistical difference between pre-operative ABR values and those obtained 10 days after the sham surgery. ($p<0.05$) 4b) The same pattern was observed in the CGP-Dex-hydrogel group. There was a 5 to 20 dB increase in hearing thresholds across frequencies in the immediate post-operative period (dashed line). By post-operative day 10, the hearing thresholds returned to baseline levels (dotted line). At the conclusion of the experiment, there was no statistical difference between pre-operative ABR values and those obtained 10 days after placement of CGP-Dex-hydrogel. ($p<0.05$). Frequencies tested are in within the normal hearing range of mice. The error bars represent the SEM

DETAILED DESCRIPTION OF THE INVENTION

This invention relates in one embodiment to a controlled release delivery composition for otorhinolaryngology and otorhinolaryngology-associated pathology, conditions, indications or their combination, Head and Neck associated pathology conditions, indications or their combination, or their combination, comprising a chitosan-glycerophosphate (CGP) hydrogel and an agent, bio-materials and their combination. In another embodiment, a composition as described herein delivers an agent at a controlled rate for an extended time. In another embodiment, the composition is localized by spatial placement near where it is needed. In another embodiment, the composition targets a drug action by using techniques known to a person of skill in the art. In another embodiment, targeting comprises delivery of a drug to a particular organ. In another embodiment, targeting comprises delivery of a drug to a particular tissue. In another embodiment, targeting comprises delivery of a drug to a particular cell type. In one embodiment, the compositions provided herein comprise a chitosan-glycerophosphate (CGP) hydrogel having a first chitosan to glycerophosphate ratio; and a chitosan-glycerophosphate (CGP) hydrogel having a second chotosan to glycerophosphate ratio, wherein the first chitosan to glycerophosphate ratio is different from the second chotosan to glycerophosphate ratio; and one or more additional agent. In one embodiment, the additional agent is a bio-material, as described hereinbelow.

In one embodiment, provided herein is a composition for controlled release delivery, comprising: a chitosan-glycerophosphate (CGP) hydrogel; and one or more agent effective for the treatment of otorhinolaryngology-associated pathology, or Head and Neck associated pathology or their combination. In another embodiment the on or more agent are bio-materials.

In another embodiment, provided herein is a method of treating an otorhinolaryngology-associated pathology, or Head and Neck associated pathology in a subject, comprising the step of inserting a composition comprising a chitosan-glycerophosphate (CGP) hydrogel and one or more agent in a predetermined region of said subject, wherein the agent is effective in the treatment of otorhinolaryngology-associated pathology, or Head and Neck associated pathology. In another embodiment the on or more agent are bio-materials.

In another embodiment, the composition controls entry to the body according to the specifications of the required drug delivery profile. In another embodiment, the composition controls the rate and duration of delivery. In another embodiment, the rate and duration of delivery are designed to achieve desired concentration.

In another embodiment, the composition is a sustained release composition. In another embodiment, a sustained release composition releases a drug over extended time. In another embodiment, rate and duration are not designed to achieve a particular profile.

In another embodiment, the composition of the invention reduced side effects because effective concentration of a drug is maintained. In another embodiment, the composition of the invention eliminates damage to non-target.

In another embodiment, the composition is in a chitosan-glycerophosphate (CGP) hydrogel form. In another embodiment, the chitosan-glycerophosphate (CGP) hydrogel serves as a drug reservoir. In another embodiment, the drug diffuses from the chitosan-glycerophosphate (CGP) hydrogel. In another embodiment, the chitosan-glycerophosphate (CGP) hydrogel comprising a drug of the invention is placed near or at the site of treatment.

In another embodiment, the drug is physically blended with the chitosan-glycerophosphate (CGP) hydrogel. In another embodiment, the drug is dissolved or dispersed within the chitosan-glycerophosphate (CGP) hydrogel. In another embodiment, the drug is uniformly dissolved or dispersed within the chitosan-glycerophosphate (CGP) hydrogel. In another embodiment, the characteristics of the chitosan-glycerophosphate (CGP) hydrogel define a drug rate-controlling mechanism. In addition, the active compounds may be incorporated into sustained-release, pulsed release, controlled release or postponed release preparations and formulations.

Controlled or sustained release compositions include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In one embodiment, the composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In another embodiment, a controlled release system can be placed in proximity to the therapeutic target, i.e., the ear nose or throat, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

In another embodiment, the chitosan-glycerophosphate (CGP) hydrogel comprises a microbead structure. In another embodiment, the chitosan-glycerophosphate (CGP) hydrogel comprises a microtube structure or a polymeric hollow fiber. In another embodiment, the chitosan-glycerophosphate (CGP) hydrogel serves as an osmotic pump.

In another embodiment, the chitosan-glycerophosphate (CGP) hydrogel is further surrounded by a polymer film that further controls the drug release rate. In another embodiment, the chitosan-glycerophosphate (CGP) hydrogel serves as a drug reservoir implant. In another embodiment, the chitosan-glycerophosphate (CGP) hydrogel comprises a rate control mechanism of solvent activation. In another embodiment, the chitosan-glycerophosphate (CGP) hydrogel absorbs fluids. In another embodiment, the chitosan-glycerophosphate (CGP) hydrogel is swollen. In another embodiment, swelling allows drug to migrate more easily. In another embodiment, water penetrates the chitosan-glycerophosphate (CGP) hydrogel thus forming pores and releasing the drug.

In another embodiment, a composition comprising chitosan-glycerophosphate (CGP) hydrogel and a drug is administered parenterally. In another embodiment, a composition comprising chitosan-glycerophosphate (CGP) hydrogel and a drug is administered by an injection. In another embodiment, a composition comprising chitosan-glycerophosphate (CGP) hydrogel and a drug is administered subcutaneously. In another embodiment, a composition comprising chitosan-glycerophosphate (CGP) hydrogel and a drug is administered intramuscularly. In another embodiment, a composition comprising chitosan-glycerophosphate (CGP) hydrogel and a drug is administered intraperitonealy. In another embodiment, a composition comprising chitosan-glycerophosphate (CGP) hydrogel and a drug is administered intravenously. In another embodiment, a composition comprising chitosan-glycerophosphate (CGP) hydrogel and a drug is administered orally. In another embodiment, a composition comprising chitosan-glycerophosphate (CGP) hydrogel and a drug bypasses some routes of metabolic clearance. In another embodiment, a composition comprising chitosan-glycerophosphate (CGP) hydrogel and a drug substantially improves patients' compliance.

In another embodiment, a composition comprising chitosan-glycerophosphate (CGP) hydrogel and a drug is accessible to an organ. In another embodiment, a composition comprising chitosan-glycerophosphate (CGP) hydrogel and a drug is accessible to a large surface area. In another embodiment, a composition comprising chitosan-glycerophosphate (CGP) hydrogel and a drug exhibits elevated absorption.

In another embodiment, a chitosan-glycerophosphate (CGP) hydrogel releases a drug over a period of 2-4 hours. In another embodiment, a chitosan-glycerophosphate (CGP) hydrogel releases a drug over a period of 3-9 hours. In another embodiment, a chitosan-glycerophosphate (CGP) hydrogel releases a drug over a period of 5-15 hours. In another embodiment, a chitosan-glycerophosphate (CGP) hydrogel releases a drug over a period of 10-20 hours. In another embodiment, a chitosan-glycerophosphate (CGP) hydrogel releases a drug over a period of 15-30 hours. In another embodiment, a chitosan-glycerophosphate (CGP) hydrogel releases a drug over a period of 25-40 hours. In another embodiment, a chitosan-glycerophosphate (CGP) hydrogel releases a drug over a period of 30-45 hours. In another embodiment, a chitosan-glycerophosphate (CGP) hydrogel releases a drug over a period of 45-60 hours. In another embodiment, a chitosan-glycerophosphate (CGP) hydrogel releases a drug over a period of 50-70 hours. In another embodiment, a chitosan-glycerophosphate (CGP) hydrogel releases a drug over a period of 60-90 hours. In another embodiment, a chitosan-glycerophosphate (CGP) hydrogel releases a drug over a period of 90-120 hours.

In another embodiment, a chitosan-glycerophosphate (CGP) hydrogel releases a drug over a period of 5-7 days. In another embodiment, a chitosan-glycerophosphate (CGP) hydrogel releases a drug over a period of 6-10 days. In another embodiment, a chitosan-glycerophosphate (CGP) hydrogel releases a drug over a period of 10-15 days. In another embodiment, a chitosan-glycerophosphate (CGP) hydrogel releases a drug over a period of 15-20 days. In another embodiment, a chitosan-glycerophosphate (CGP) hydrogel releases a drug over a period of 20-30 days. In another embodiment, a chitosan-glycerophosphate (CGP) hydrogel releases a drug over a period of 30-45 days. In another embodiment, a chitosan-glycerophosphate (CGP) hydrogel releases a drug over a period of 45-90 days. In another embodiment, a chitosan-glycerophosphate (CGP) hydrogel releases a drug over a period of 90-120 days. In another embodiment, a chitosan-glycerophosphate (CGP) hydrogel releases a drug over a period of 100-200 days. In another embodiment, a chitosan-glycerophosphate (CGP) hydrogel releases a drug over a period of 200-370 days.

In another embodiment, a chitosan-glycerophosphate (CGP) hydrogel releases a drug over a period of 1-1.5 years. In another embodiment, a chitosan-glycerophosphate (CGP) hydrogel releases a drug over a period of 1-2 years. In another embodiment, a chitosan-glycerophosphate (CGP) hydrogel releases a drug over a period of 1.5-3 years.

In another embodiment, a chitosan-glycerophosphate (CGP) hydrogel composition of the invention comprises a drug or a bioactive agent. In another embodiment, the term drug comprises a bioactive agent. In another embodiment, a chitosan-glycerophosphate (CGP) hydrogel composition of the invention treats an Otorhinolaryngology-associated pathology. In another embodiment, the CGP comprising compositions described herein, treats Head and Neck associated pathology. In another embodiment, a chitosan-glycerophosphate (CGP) hydrogel composition of the invention prevents an Otorhinolaryngology-associated pathology, Head and Neck associated pathology or their combination. In another embodiment, a chitosan-glycerophosphate (CGP) hydrogel composition of the invention inhibits an Otorhinolaryngology-associated pathology, Head and Neck associated pathology or their combination. In another embodiment, a chitosan-glycerophosphate (CGP) hydrogel composition of the invention improves the condition of a patient affected with an Otorhinolaryngology-associated pathology, Head and Neck associated pathology or their combination.

In another embodiment, the Otorhinolaryngology-associated pathology is hearing loss. In another embodiment, the Otorhinolaryngology-associated pathology is vertigo. In another embodiment, the Otorhinolaryngology-associated pathology is a vestibular Disorder. In another embodiment, the Otorhinolaryngology-associated pathology is an ear infection. In another embodiment, the Otorhinolaryngology-associated pathology is Otitis Media. In another embodiment, the Otorhinolaryngology-associated pathology is a sinus infections or a sinus disease. In another embodiment, the Otorhinolaryngology-associated pathology is scaring or stenosis of openings within the ear and sinuses. In another embodiment, the Otorhinolaryngology-associated pathology is a cancer associted with the head and neck. In another embodiment, the Otorhinolaryngology-associated pathology comprises an abscess or an infections of the ear, nose, throat, head, neck, or a combination thereof. In another embodiment, the Otorhinolaryngology-associated pathology comprises otology pathology. In another embodiment, the Otorhinolaryngology-associated pathology comprises neurotology pathology. In another embodiment, the Otorhinolaryngology-associated pathology comprises rhinology pathology. In another embodiment, the Otorhinolaryngology-associated pathology comprises an allergy. In another embodiment, the Otorhinolaryngology-associated pathology comprises laryngology pathology. In another embodiment, the Otorhinolaryngology-associated pathology comprises bronchoesophagology pathology.

In one embodiment, Head and Neck associated pathology is Branchial Cleft Cyst. Or in another embodiment, the Head and Neck associated pathology is a salivary-gland associated pathology, a thyroid-associated pathology, Verrucal Keratosis of the larynx or their combination in certain other embodiment. In one embodiment, Head and Neck-associated pathology, refers to any pathology associated with the head, neck or organs or tissue comprised in the head and neck, each of which, is a discrete embodiment to be treated with the methods and compositions described herein.

In another embodiment, the terms active pharmaceutical ingredient, agent, and drug are used interchangeably. In another embodiment, the agent is a steroid. In another embodiment, the agent is an antibiotic agent. In another embodiment, the agent is an antiviral agent. In another embodiment, the agent is a fungicidal. In another embodiment, the agent is a neurological agent. In one embodiment, the agent is non-steroidal anti-inflammatory agent.

In another embodiment, the agent is dexamethasone. In another embodiment, the agent is acetic acid. In another embodiment, the agent is acetic acid-aluminum acetate. In another embodiment, the agent is hydrocortisone. In another embodiment, the agent is hydrocortisone-acetic acid. In another embodiment, the agent is benzocaine. In another embodiment, the agent is benzotic. In another embodiment, the agent is floxin. In another embodiment, the agent is ciprodex. In another embodiment, the agent is cipro. In another embodiment, the agent is flunisolide. In another embodiment, the agent is fluticasone. In another embodiment, the agent is mometasone. In another embodiment, the agent is ipratropium. In another embodiment, the agent is beconase. In another embodiment, the agent is triamcinolone. In another embodiment, the agent is chlorhexidine gluconate. In another embodiment, the agent is doxycycline. . In another embodiment, the agent is pilocarpine. In another embodiment, the agent is levocabastine. In another embodiment, the agent is sodium cromoglycate. In another embodiment, the agent is bacitracin zinc. In another embodiment, the agent is polymyxin B-sulfate. In another embodiment, the agent is chloramphenicol. In another embodiment, the agent is erythromycin.

In another embodiment, the agent is levocabastine HCl. In another embodiment, the agent is ciprofloxacin HCl. In another embodiment, the agent is ciprofloxacin HCl/hydrocortisone. In another embodiment, the agent is erythromycin. In another embodiment, the agent is framycetin sulfate. In another embodiment, the agent is gramicidin. In another embodiment, the agent is gentamicin sulfate. In another embodiment, the agent is gramicidin. In another embodiment, the agent is neomycin sulfate. In another embodiment, the agent is ofloxacin. In another embodiment, the agent is trimethoprim sulfate. In another embodiment, the agent is sulfacetamide sodium. In another embodiment, the agent is tobramycin trifluridine. In another embodiment, the agent is beclomethasone dipropionate. In another embodiment, the agent is betamethasone sodium phosphate. In another embodiment, the agent is budesonide. In another embodiment, the agent is clioquinol. In another embodiment, the agent is fluorometholone. In another embodiment, the agent is fluorometholone acetate. In another embodiment, the agent is prednisolone acetate. In another embodiment, the agent is triamcinolone acetonide. In another embodiment, the agent is diclofenac sodium. In another embodiment, the agent is flurbiprofen sodium In another embodiment, the agent is atropine sulfate. In another embodiment, the agent is cyclopentolate HCl. In another embodiment, the agent is dipivefrin HCl. In another embodiment, the agent is homatropine Hbr. In another embodiment, the agent is benzydamine HCl In another embodiment, the agent is antazoline phosphate. In another embodiment, the agent is naphazoline HCl. In another embodiment, the agent is phenylephrine HCl. In another embodiment, the agent is brimonidine tartrate. In another embodiment, the agent is timolol maleate. In another embodiment, the agent is betaxolol HCl. In another embodiment, the agent is dipivefrin HCl. In another embodiment, the agent is levobunolol HCl. In another embodiment, the agent is acetazolamide brinzolamide. In another embodiment, the agent is dorzolamide HCl In another embodiment, the agent is carbachol. In another embodiment, the agent is pilocarpine HCl. In another embodiment, the agent is bimatoprost. In another embodiment, the agent is latanoprost. In another embodiment, the agent is travoprost. In another embodiment, the agent is apraclonidine HCl.

In another embodiment, the agent is an adrenocorticoids such as but not limited to betamethasone, cortisone, dexamethasone, hydrocortisone, methylprednisolone, paramethasone, prednisolone, prednisone, and triamcinolone. Exemplary analgesics include acetaminophen, aspirin, buprenorphine, butalbital, butorphanol, codeine, dezocine, diflunisal, dihydrocodeine, etodolac, fenoprefen, fentanyl, floctafenine, hydrocodone, hydromorphone, ibuprofen, ketoprofen, ketorolac, levorphanol, magnesium salicylate, meclofenamate, mefenamic acid, meperidine, meprobamate, methadone, methotrimeprazine, morphine, nalbuphine, naproxen, opium, oxycodone, oxymorphone, pentazocine, phenobarbital, propoxyphene, salsalate, and sodium salicylate. One exemplary analgesic adjunct is caffeine. Exemplary anesthetics include articane-epinephrine, bupivacaine, chloroprocaine, etidocaine, ketamine, lidocaine, mepivacaine, methohexital, prilocaine, propofol, propoxycaine, tetracaine, and thiopental. One exemplary analgesic-anesthetic is antipyrine-benzocaine.

In another embodiment, the agent is an antibiotic such as but not limited to anti-bacterials, and anti-infectives include sulfonamides (e.g., sulfanilamide, sulfadiazine, sulfamethoxazole, sulfisoxazole, para-aminobenzoic acid, or sulfacetamide), trimethoprim-sulfamethoxazole, quinolones (e.g., ciprofloxacin, ofloxacin, or nalidixic acid), .beta.-lactam antibiotics such as penicillins or cephalosporins, aminoglycosides (e.g., kanamycin, tobromycin, gentamycin C, amikacin, neomycin, netilmicin, streptomycin, or vancomycin), tetracyclines, chloramphenicol, and macrolides (e.g., erythromycin, clarithromycin, or azithromycin). Non-limiting examples of suitable penicillins include penicillin G, penicillin V, methicillin, oxacillin, nafeillin, ampicillin, and amoxicillin Non-limiting examples of suitable cephalosporins include cephalothin, cefdinir, cefozolin, cephalexin, cefadraxal, cefamandole, cefoxitin, cefaclor, cefonicid, cefoletan, cefotaxime, ceftizoxime, cefrtriaxone, cefditoren, and cefepine. Exemplary antibiotics useful for treating OM include penicillins such as amoxicillin and amoxicillin-clavulanate (Augmentin®); sulfa-based combinations such as erythromycin-sulfisoxazole (Pediazole), trimethoprim-sulfamethoxazole (Bactrim, Septra®); macrolides/azalides such as azithromycin (Zithromax®) or clarithromycin (Biaxin®); second-generation cephalosporins such as cefaclor (Ceclor®), cefprozil (Cefzil®), cefuroxime axetil (Ceftin®), or loracarbef (Lorabid®); and third generation cephalosporins such as cefdinir (Omnicef®), cefixime (Suprax®), cefpodoxime proxetil (Vantin®), ceftibuten (Cedax®), cefditoren (Spectracef,®), and ceftriaxone (Rocephin®).

In another embodiment, the agent is an anti-emetic such as but not limited to buclizine, chlorpromazine, cyclizine, dimenhydrinate, diphenhydramine, diphenidol, domperidone, dronabinol, haloperidol, hydroxyzine, meclizine, metoclopramine, nabilone, ondansetron, perphenazine, prochlorperazine, promethazine, scopolamine, thiethylperazine, triflupromazine, and trimethobenzamine. Exemplary antifungals include amphotericin B, clioquinol, clotrimazole, fluconazole, flucytosine, griseofulvin, ketoconazole, miconazole, and potassium iodide. Exemplary anti-inflammatory agents include aluminum acetate, aspirin, betamethasone, bufexamac, celecoxib, dexamethasone, diclofenac, etodolac, flurbiprofen, hydrocortisone, indomethacin, magnesium salicylate, naproxen, prednisolone, rofecoxib, salsalate, sulindac, and triamcinolone. Exemplary anti-vertigo agents suitable for the invention include belladonna, dimenhydrinate, diphenhydramine, diphenidol, meclizine, promethazine, and scopolamine Exemplary anti-viral agents suitable for the invention include acyclovir, amantadine, delavirdine, didanosine, efavirenz, foscamet, ganciclovir, indinavir, nelfinavir, ribavirin, ritonavir, zalcitabine, and zidovudine. Exemplary biological response modifiers include aldesleukin, interferon .alpha.-2a, interferon .alpha.-2b, interferon .alpha.-n1, interferon .alpha.-n3, interferon .gamma., and levamisole. Exemplary cytotoxic agents include podofilox and podophyllum. Exemplary immunizing agents include influenza virus vaccine, pneumococcal vaccine polyvalent, and immune globulin. An exemplary immunomodulator invention is interferon .gamma. Other pharmacologic agents suitable for the invention include betahistine (e.g., for treating the nausea, dizziness, and ringing in the ears that occur in Meniere's disease), prochlorperazine, and hyoscine.

In another embodiment, the agent is chlorhexidine gluconate.

In another embodiment, the composition comprises 0.5-40% (w/w) chitosan. In another embodiment, the composition comprises 1-5% (w/w) chitosan. In another embodiment, the composition comprises 2-8% (w/w) chitosan. In another embodiment, the composition comprises 5-10% (w/w) chitosan. In another embodiment, the composition comprises 8-12% (w/w) chitosan. In another embodiment, the composition comprises 12-20% (w/w) chitosan. In another embodiment, the composition comprises 15-25% (w/w) chitosan. In another embodiment, the composition comprises 20-30% (w/w) chitosan. In another embodiment, the composition comprises 25-35% (w/w) chitosan. In another embodiment, the composition comprises 30-40% (w/w) chitosan.

In another embodiment, the composition comprises 1-60% (w/w) glycerophosphate. In another embodiment, the composition comprises 1-5% (w/w) glycerophosphate. In another embodiment, the composition comprises 5-15% (w/w) glycerophosphate. In another embodiment, the composition comprises 10-20% (w/w) glycerophosphate. In another embodiment, the composition comprises 15-25% (w/w) glycerophosphate. In another embodiment, the composition comprises 20-30% (w/w) glycerophosphate. In another embodiment, the composition comprises 25-35% (w/w) glycerophosphate. In another embodiment, the composition comprises 35-45% (w/w) glycerophosphate. In another embodiment, the composition comprises 40-50% (w/w) glycerophosphate. In another embodiment, the composition comprises 50-60% (w/w) glycerophosphate.

In another embodiment, the composition is in a solid form. In another embodiment, the composition is in a liquid form. In another embodiment, the composition is in a gel form. In another embodiment, the composition is in a semi-gel form. In another embodiment, the composition's form is determined by factors comprising the ratio of glycerophosphate to chitosan. In another embodiment, the composition's the agent release profile is determined by factors comprising the ratio of glycerophosphate to chitosan. In another embodiment, the higher the ratio of chitosan to glycerophosphate when the agent is hydrophilic, the longer is the agent release following the initial release. In another embodiment, the lower the ratio of chitosan to glycerophosphate when the agent is hydrophobic, the longer is the agent release following the initial release.

In another embodiment, by altering the composition of CGP-hydrogel the physical properties can be adjusted to fit various release strategies. In another embodiment, these properties comprise the diameter of pores in the matrix, the strength of the matrix and the rate of matrix degradation. In another embodiment, by altering the pore size, the initial volume of drug released is controlled as a bolus early in the treatment course. In another embodiment, the mechanical strength of the CGP-hydrogel is fortified by adjusting the proportions of the hydrogel components permitting the design of hydrogels with reduced susceptibility to degradation, thereby prolonging the release of drug. In another embodiment, susceptibility of CGP-hydrogel to degradation by lysozyme is also adjustable which further enables us to fine tune the drug release properties of this system for the specific requirements of a given clinical scenario.

In another embodiment, the composition comprises at least two different chitosan to glycerophosphate ratio. In another embodiment, the composition comprises two different chitosan to glycerophosphate ratio. In another embodiment, the composition comprises three different chitosan to glycerophosphate ratio. In another embodiment, the composition comprises four different chitosan to glycerophosphate ratio. In another embodiment, the composition comprises five different chitosan to glycerophosphate ratio. In another embodiment, the composition comprises six different chitosan to glycerophosphate ratio.

In another embodiment, the invention provides a method of treating an Otorhinolaryngology-associated pathology in a subject, comprising the step of administering a composition comprising a chitosan-glycerophosphate (CGP) hydrogel and an agent, bio-materials and their combination in a predetermined region in a subject. In anther embodiment, the method comprises topical administration. In another embodiment, the method comprises trans-tympanic administration. In another embodiment, the method comprises intra-tympanic administration. In another embodiment, the method comprises intraperitoneal administration. In another embodiment, the method comprises intravenous administration. In another embodiment, the method comprises intramascular administration. In another embodiment, the method comprises intra-ear administration. In another embodiment, the method comprises administration into the Round Window Niche (RWN). Bio-material refers in one embodiment, to any material in addition to the active pharmaceutical ingredient (API) or the agent used in the methods and compositions described herein, which is beneficial in the treatment of Otorhinolaryngology-associated pathology in a subject, such as an abscess in one embodiment or infections of the ear, nose, throat, head, neck, or a combination thereof in other discrete embodiments. In another embodiment, the bio-material is antibiotics, or antivirals, antifungals, anesthetics, anti-inflammatory agents, anti-allergic agents, penetration enhancement agents, wetting agents, surface active agents, diluents, viscosity enhancing agents, chemotherapeutic agents, or their combination in other discrete embodiments of the biomaterials used in the controlled release compositions described herein.

In another embodiment, the method comprises administering the composition of the invention in a solid state. In another embodiment, the method comprises adminstering the composition of the invention in a liquid state. In another embodiment, the method comprises adminstering the composition of the invention in a gel form. In another embodiment, the invention provides that the composition's states of aggregation changes from a liquid to a semi-solid gel when maintained in a temperature of 36° C. to 38° C. In another embodiment, the method comprises adminstering the composition in a semi-solid gel form. In another embodiment, the method provides that a semi-solid gel form is preserved in a subject's body temperature.

In another embodiment, the method comprises topically administering the composition of the invention onto an affected area. In another embodiment, the method comprises locally injecting the composition of the invention under the integument of an affected area.

In another embodiment, hydrogels of the invention are suitable for use in the subject methods because they are biocompatible, by which is meant that they are suitable for contact with a human tissue.

In another embodiment, the hydrogel further comprises macromolecular or polymeric materials into which water and small molecules can easily diffuse and include hydrogels prepared through the cross linking. In another embodiment, crosslinking may be either through covalent, ionic or hydrophobic bonds introduced through use of either chemical cross-linking agents or electromagnetic radiation, such as ultraviolet light, of both natural and synthetic hydrophilic polymers, including homo and co-polymers. In another embodiment, additional hydrogels of interest include those prepared through the cross-linking of: polyethers, e.g. polyakyleneoxides such as poly(ethylene glycol), poly(ethylene oxide), poly(ethylene oxide)-co-(poly(propyleneoxide) block copolymers; poly(vinyl alcohol); poly(vinyl pyrrolidone); polysaccharides, e.g. hyaluronic acid, dextran, chondroitin sulfate, heparin, heparin sulfate or alginate; proteins, e.g. gelatin, collagen, albumin, ovalbumin or polyamino acids; and the like.

In another embodiment, the physical characteristics such as size, shape and surface area can affect the absorption and release characteristics of the hydrogel composition. In another embodiment, the hydrogel composition that is employed may be in a variety of configurations, including particles, beads, rods, sheets, irregular shapes and the like.

In another embodiment, the hydrogel shape comprises greater surface area to total mass ratios. In another embodiment, the porosity of the hydrogel affects the absorption and release characteristics of the hydrogel.

In another embodiment, the amount of pharmacologic agent present in the composition is dependent on the type of pharmacologic agent and its known effective dosage. In another embodiment, as described hereinabove a composition can include any type of pharmacologic agent, including, e.g., an adrenocorticoid (corticosteroid, steroid), analgesic, analgesic adjunct, analgesic-anesthetic, anesthetic, antibiotic, antibacterial, anti-infective, antibiotic therapy adjunct, antidote, anti-emetic, anti-fungal, antiinflammatory, antivertigo, anti-viral, biological response modifier, cytotoxic, diagnostic aid, immunizing agent, immunomodulator, proteins, peptides, and other agents that may useful in treating ear disorders. Analgesic, analgesic adjunct, analgesic-anesthetic, anesthetic, antibiotic, antibacterial, anti-infective, antibiotic therapy adjunct, anti-fungal, anti-inflammatory, anti-viral, and peptides are particularly useful.

In another embodiment, a composition of the invention can include a plurality of pharmacologic agents, including two or more agents within the same class (e.g., two different antibiotics) or two or more agents of various types, depending on the effect desired. For example, to fight a bacterial infection, to reduce tissue inflammation, and to alleviate irritation, a composition can contain an antibacterial, an anti-inflammatory, and an anesthetic or analgesic. In another embodiment, those skilled in the art can identify pharmacologic agents and combine them as needed to achieve a desired effect.

To further tailor the binding properties of the hydrogel, in another embodiment, the hydrogel can be modified to provide for specific binding of one or more of the agents to the surface of the hydrogel. In another embodiment, the hydrogel comprises agents that act as water absorbents and/or precipitants, where such agents include ethanol, PEG 400, phosphate buffer and the like.

In another embodiment, the hydrogel compositions employed in the subject methods can be prepared by methods known to those skilled in the art.

The term "about" as used herein means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Materials and Methods:
Biodegradable Hydrogel Preparation

The parameters for formulating the CGP-hydrogel loaded with dexamethasone were selected creating a model formulation for further testing (CGP-Dex-hydrogel). The CGP-Dex-hydrogel was moderately viscous, injectable, and underwent phase transition to a semi-solid gel in about 15 minutes at 37° C. Preparations were made on the day in which they were to be used. Ninety-eight percent deacetylated chitosan (Biosyntech, Québec) was dissolved in 0.2M acetic acid yielding a 3.4% (w/w) chitosan solution. To this solution, water soluble dexamethasone 0.7% (w/w) (D2915, Sigma, St. Louis Mo.) and glycreophosphate (G6501, Sigma, St. Louis Mo.) 9% (w/w) were added. CGP-hydrogel was prepared and maintained at room temperature until it was used.

In Vitro Matrix Degradation and Dexamethasone Release CGP-Dex-Hydrogel Pellet Preparation:

In order to evaluate CGP-Dex-hydrogel drug release and matrix degradation in the in vitro setting, it was necessary to create uniform samples which could be handled and transferred. To achieve this purpose, solidified CGP-Dex-hydrogel pellets were created. Liquid CGP-hydrogel was allowed to solidify in 1-ml syringes at 37° C. for two hours until solidified. The tips of the syringes were clipped off with a razor and columns of gel were gently extruded. By sectioning these gel columns at 0.1 ml increments, hydrogel pellets were created.

Dexamethasone Release from CGP-Dex-Hydrogel:

An in vitro drug release study was designed to evaluate the release of dexamethasone from the CGP-dex-hydrogel pellets. Individual CGP-Dex-hydrogel pellets were placed into 2-ml microcentrifuge tubes, weighed, and immediately loaded with 1 ml Dulbecco's phosphate buffered saline (PBS). The microcentrifuge tubes were then incubated at 37° C. on a shaker table at 100 rpm. Every 24 hours the pellets were gently removed from the PBS solution and placed into fresh sets of microcentrifuge tubes with 1 ml PBS and incubated as before. The PBS sample solution was collected, 1 ml of 50% ethanol was added and the samples were then stored at 4° C. until analysis by UV spectrophotometry.

Degradation of CGP-Dex-Hydrogel:

To understand the relationship between the release of dexamethasone and the degradation of the CGP-Dex-hydrogel matrix, the conditions of the dexamethasone release experiment were repeated. However, the pellets were collected every 24 hours for 4 days. After collection the pellets were desiccated for 72 hours and weighed. The ratio of solid components remaining was derived by subtracting from the starting pellet weight, the water weight of each pellet which was calculated from the CGP-Dex-hydrogel formula. A ratio was calculated between the initial solid component weight and the ending solid component weight for samples obtained daily over a 4 day period.

In Vivo Dexamethasone Release and Auditory Function Assessment

Experimental Animals:

To assess the CGP-Dex-hydrogel mediated release of dexamethasone in vivo and to assess the safety of this system in an in vivo setting, an animal model was constructed. C57BL/6J mice (Charles River, Wilmington, Mass.) of either sex and weighing 18 to 22 g were used at 6 to 8 weeks of age. Animals care and use was in accordance with the Institutional Animal Care and Use Committee of the University of Pennsylvania. Anesthetic used for all experiments was tribromoethanol. In total, 25 mice were used. The mice were divided into two groups a CGP-Dex-hydrogel placement group (n=20) and a sham surgery group (n=5). Fifteen of the mice in the CGP-Dex-hydrogel placement group were used for quantification of dexamethasone. The remaining 5 mice from this group and the 5 mice from the sham surgery group were used to evaluate the impact of the surgical procedure and of CGP-Dex-hydrogel upon the auditory system.

CGP-Dex-Hydrogel Placement Procedure:

In preparation for detection of dexamethasone in murine perilymph after CGP-Dex-hydrogel placement, a procedure for placement of CGP-Dex-hydrogel was devised. On the left side, a 2 cm post-auricular incision was made and dissection was carried out along the external auditory canal to the bulla. A 1 mm diamond burr was used to create a single burr hole through the bulla just posterior and inferior to the facial nerve. Through this control-hole, the intact stapedial artery and the round window niche and membrane were visualized. Twenty five mice underwent the surgical procedure to this point. For five of the mice (sham surgery group) the incision was then closed and the animals were allowed to recover. For the remaining 20 mice, CGP-Dex-hydrogel was injected directly onto the RWM filling the RWN. The injection was accomplished with the use of a custom-made flame-pulled glass syringe needle using a microcapillary tube flame-puller. The skin incisions were closed with 4-0 silk, and the animals were returned to the animal facility after they fully recovered from the anesthetic agent.

Perilymph and Serum Harvesting Procedures:

Fifteen of the animals which underwent surgical placement of CGP-Dex-Hydrogel were separated into three groups of 5 animals each for sample harvesting on post-operative days 1, 3 and 5. At the time of sample collection, mice were deeply anesthetized. A cardiac puncture was performed to obtain blood for serum drug concentration analysis. The skin overlying the skull was removed and the external auditory canals were transected. Using a pick and fine forceps the tympanic membrane of the left ear was gently removed. The stapes and oval window were exposed after removing the malleus and incus. Perilymph was collected in previously prepared microcapillary tubes which had tips drawn to approximately 20 pm. The tip of the glass microcapillary tube was used to gently displace the footplate of the stapes laterally. The tip of the microcapillary tube was then advanced a few micrometers through the annular ligament and into the scala vestibule. Via capillary action, within a few seconds a target volume of 0.2 to 0.3 µl of perilymph was collected into the capillary tube. Following this, each animal was euthanized by cervical dislocation. Perilymph was transferred to microcentrifuge tubes and weighed to within 0.01 mg. One mg of perilymph corresponded to 1 µl of perilymph. Samples were stored at −80° C. until they were analyzed.

In order to obtain perilymph samples for analysis, a procedure to collect consistent small sample sizes of perilymph was created. Special attention to collection methods is necessary to insure the quality of data generated. This is because in mice one must consider the potential which exists for contamination of perilymph samples with cerebrospinal fluid. This contamination can potentially occur because of an existing anatomical communication with the CSF space, the cochlear aqueduct. In mice and lower mammals, the cochlear aqueduct remains patent, this is not normally the case for humans To prevent skewed data as a result of contamination we devised a way to rapidly harvest perilymph in consistent volumes which was well below the average volume of the perilymphatic space in our murine model.

Dexamethasone Concentration in Perilymph and Serum::

To elucidate whether dexamethasone was released into murine perilymph after surgical placement of CGP-Dex-hydrogel and the time-based release kinetics, we analyzed the harvested perilymph samples by liquid chromatography (LC) and mass spectroscopy (MS). Also, to prove that the concentration of dexamethasone was elevated in the local environment compared to systemic distribution, serum samples were also analyzed by LC/MS for comparison. Harvested perilymph and serum samples were analyzed using a Finnigan LTQ linear ion trap mass spectrometer (Thermo Fisher Waltham, Mass.) equipped with an electrospray ionization source. LC separations were conducted with a Zorbax 300 Extend-C18 column (125 Å, 3.5μ, 150×2.1 mm i.d., Agilent Santa Clara, Calif.) using a linear gradient of 5 mM ammonium acetate in water-methanol with a flow rate of 250 μl/min Perilymph and serum samples were added with flumethasone (F9507 Sigma St. Louis, Mo.) as an internal standard. The sample cleanup was performed with liquid-liquid extraction using ethyl acetate. LC-MS/MS analyses were conducted using positive electrospray ionization in the monitoring MRM mode using following ion transitions: m/z 393.2→373.1 (dexamethasone), m/z 411.2→391.1 (flumethasone).

Auditory Function Assessment

To address the safety of CGP-Dex-hydrogel and the procedure to apply the hydrogel an assessment of auditory function using the auditory brainstem response (ABR) was performed to compare thresholds at three timepoints: pre-operative, immediate post-operative (post-op day 2) and late post-operative periods (post-op day 10). ABRs were recorded using a Tucker Davis System II (Tucker-Davis Technologies, Alachua, Fla.). Ten mice were divided into two groups, a CGP-Dex-hydrogel group (n=5) and sham surgery group (n=5). One animal was lost from the sham surgery group before testing on the final day of the experiment. Mice were anesthetized and electrodes were placed at the vertex (active), in the neighborhood of the left postauricular bulla (reference), and in the flank (ground). The acoustic stimulus, generated by the TDT SigGen system consisted of 10 msec tone pips at 16.0 kHz, 24.0 kHz, 32.0 kHz, and 40.0 kHz presented at a rate of 20/sec Responses were averaged over 500 stimuli and intensity increments were set at 5 dB. Threshold was determined to be halfway between the intensity at which an observable response could be detected and the next lower intensity at which no response was visible. Absolute stimulus intensities were calibrated to obtain the sound pressure level in dB relative to 20 μPa.

Statistical Analysis

Statistical analysis was performed with Statmost (Dataxiom Software, Los Angeles, Calif.). The data presented represent the mean of each group+/−standard error of the mean. The statistical test of significance was the Mann-Whitney U test. A conservative probability (P) value less than 0.01 was considered to be statistically significant.

EXAMPLE 1

In Vitro Matrix Degradation and Dexamethasone Release

Figure 1:
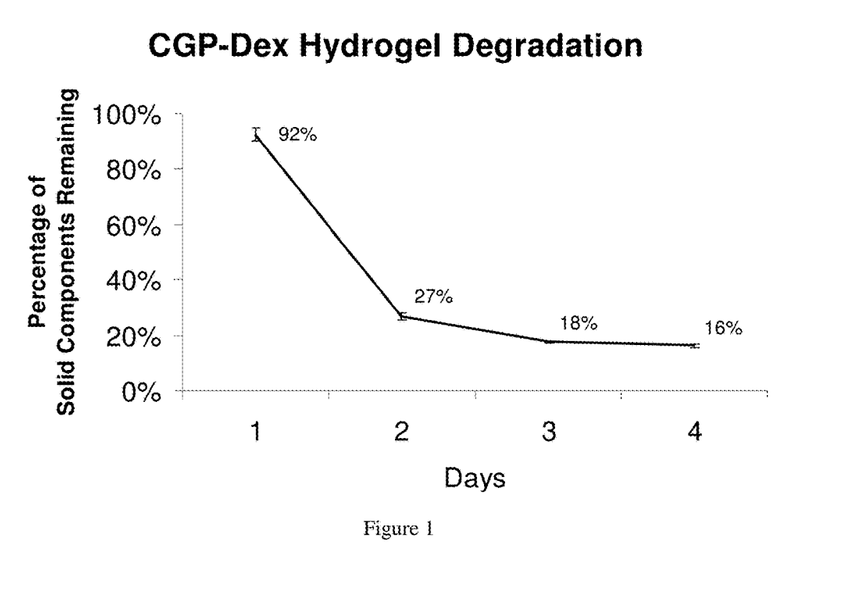
FIG. 1 shows how CGP-Dex-Hydrogel degrades in a controlled Manner. 16% of solid CGP-Dex-hydrogel remains after 4 days. The degradation of CGP-Dex-hydrogel is controlled and is tapered. The error bars represent the SEM (±0.002 to 0.026)

Degradation of CGP-Dex-Hydrogel: In vitro experiments demonstrated that 92% of the solid hydrogel matrix remained at 24 hours and then slowly degraded to 16% of the original solid component by day 4. These experiments were duplicated and the average results were plotted (FIG. 1). Results were consistent between experiments with 2.6%<SEM>0.02%.

Figure 2:
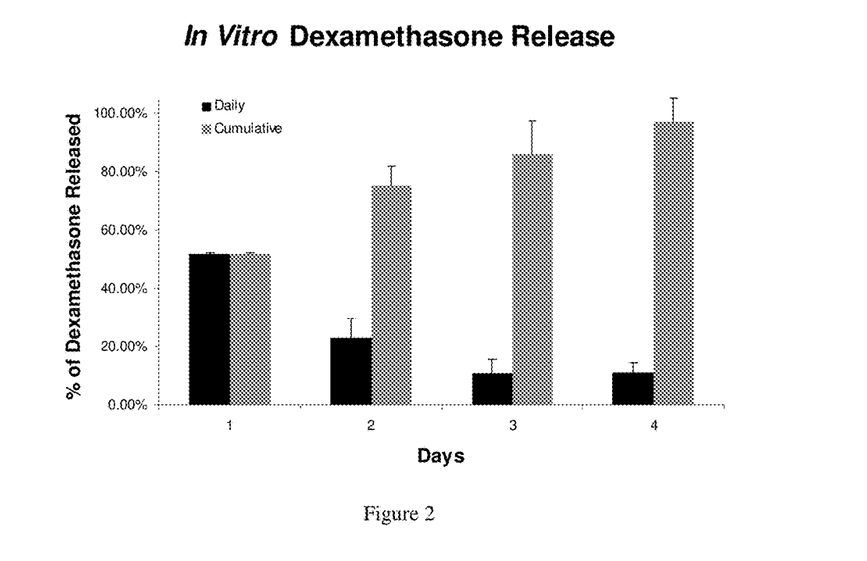
FIG. 2 shows CGP-Dex-Hydrogel release of dexamethasone in a Controlled Manner. Release of dexamethasone occurs for 4 days. The black bars represent the daily measurement and the gray bars the accumulation over the 4 days of testing. There is an initial bolus release of dexamethasone in the first 24 hours followed by a tapering off over the next three days so that by day 4 ~100% of the available dexamethasone has been released. The error bars represent the SEM (+/−0.004 to 0.114)

Dexamethasone release from CGP-Dex-hydrogel: Sustained release of dexamethasone was observed over 4 days in vitro. In the first 24-hour period there was an initial bolus release of dexamethasone followed by a tapering of drug release until 100% of the drug was released by day 4. The experiment was repeated and the average results were plotted (FIG. 2). The initial bolus release of dexamethasone is likely due to the release of dexamethasone from the voids formed in the hydrogel matrix while the gel was solidifying. The dexamethasone released over the next 3 days represents drug that was interacting more tightly with the matrix through non-covalent molecular interactions. Results were consistent between experiments with 11.4%<SEM>+/−0.04%

EXAMPLE 2

In Vivo Dexamethasone Release and Auditory Function Assessment

CGP-Dex-Hydrogel Placement Procedure: Twenty five animals successfully underwent the procedure; 20 received CGP-Dex-hydrogel and 5 received no hydrogel injection (sham surgery). There were no surgical complications, the animals recovered normally and there were no infections. Following recovery and for the duration of the experiments, no animals exhibited signs of distress nor were there were no observable pathologic changes in behavior, such as log rolling or circling, indicating that both vestibular and auditory functions were preserved.

Perilymph and Serum Harvesting Procedures: The mean volume of perilymph harvested was 0.22 μl+/−0.07 μl. There were no statistical differences between groups or between the averages of all samples (p>0.05). Day 1: 0.25 μl+/−0.07 μl; Day 3: 0.20 μl+/−0.06 μl; Day 5: 0.22 μl+/−0.07 μl. The volume of serum harvested for each animal was 5 μl.

Figure 3:
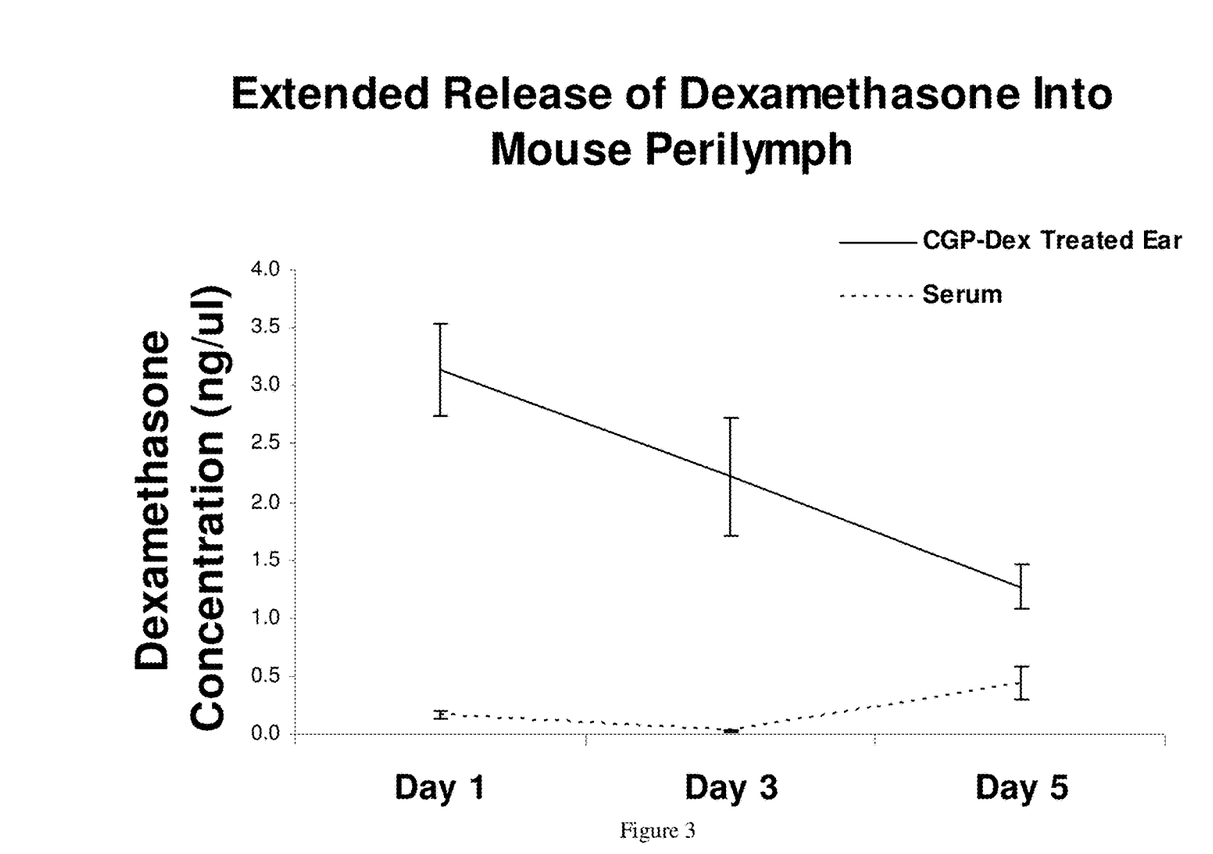
FIG. 3 shows CGP-Dex-Hydrogel locally delivery of Dexamethasone into Perilymph. The release of dexamethasone into perilymph was detected for 5 days. There was a significant difference between dexamethasone levels detected in the treated ear and serum for all time points. (Day 1 and 3 $p<0.01$ Day 5 $p<0.05$) The error bars represent the SEM (+/−0.002 to 0.509)

Dexamethasone Concentration in Perilymph and Serum: Dexamethasone was detected in the perilymph of treated ears. The average dexamethasone concentration within the perilymph peaked at 24 hours at 3.2 ng/μl and declined in a linear fashion over the 5 days of the experiment to 1.3 ng/μl. These values remained elevated compared to serum (FIG. 3). There was statistical significance between detected dexamethasone levels of the treated ear and serum of animals for all time points (Day 1 and 3 p<0.01 Day 5 p<0.05).

Figure 4:
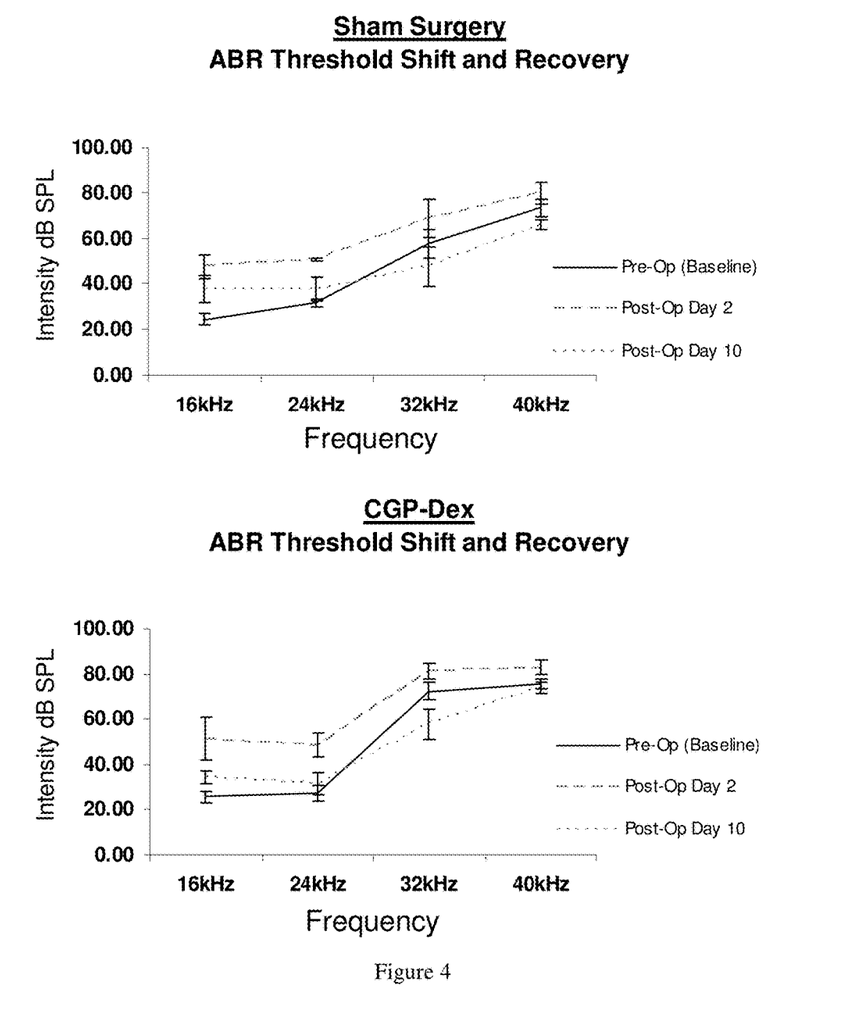

Auditory Function Assessment: There was an initial increase in ABR thresholds followed by recovery of auditory function in both the sham surgery and the CGP-Dex-hydrogel placement groups. (FIGS. 4a and 4b). The pure-tone average at pre-treatment testing across all 4 frequencies tested for the sham surgery group (n=5) and CGP-Dex-hydrogel groups (n=5) respectively were 46.7 and 50.2 dB SPL. Measurement at post-operative day 2 showed a 15.1 and 15.8 dB SPL elevation in hearing threshold for the sham surgery and CGP-Dex-hydrogel groups. By post-operative day 10, the hearing thresholds returned to baseline levels 47.2 for the sham surgery group (n=4) and 49.5 for the CGP-Dex-hydrogel group (n=5). There was no statistical difference between post-operative day 10 measurements and the pre-treatment baseline levels p>0.05. There was no statistically significant difference between hearing thresholds of the sham surgery and CGP-Dex-hydrogel groups at any tested frequency with the exception of the measurement at 40 kHz where there was a slight difference (p<0.05). One animal from the sham surgery group was lost due to anesthetic overdose at the time of testing on post-operative day 10.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of treating an otorhinolaryngology-associated pathology, or Head and Neck associated pathology in a subject, comprising administering through the auditory bulla a composition onto the round window membrane of the subject for release of an agent to the perilymph of the inner ear of the subject, wherein said composition comprises a solution of chitosan-glycerophosphate (CGP) and the agent, wherein the agent dissolved therein is present in an amount effective in the treatment of the otorhinolaryngology-associated pathology, or Head and Neck associated pathology, wherein auditory functions are preserved by said administering.

2. The method of claim 1, whereby said composition comprises 2-10% (w/w) chitosan.

3. The method of claim 1, whereby said composition comprises 5-30% (w/w) glycerophosphate.

4. The method of claim 1, whereby said composition is a controlled release composition.

5. The method of claim 4, whereby said composition releases said agent over a period of no less than 24 hours.

6. The method of claim 4, whereby a release profile is adjusted by varying a ratio of chitosan to glycerophosphate macromonomers.

7. The method of claim 6, whereby, when the agent is hydrophilic, the higher the ratio of chitosan to glycerophosphate macromonomers, the longer is the agent release following the initial release.

8. The method of claim 6, whereby, when the agent is hydrophobic, the lower the ratio of chitosan to glycerophosphate macromonomers, the, longer is the agent release following the initial release.

9. The method of claim 1, whereby the Otorhinolaryngology-associated pathology includes the diseases of otology, neurotology, rhinology, allergy, laryngology, bronchoesophagology, head and neck.

10. The method of claim 1, wherein the agent is Dexamethasone.

11. The method of claim 4, wherein the agent is released to the subject for one to four days.

12. The method of claim 1, wherein the pathology is vertigo.

13. The method of claim 1, wherein the pathology is Ménière's disease.

* * * * *